United States Patent
Albert

(10) Patent No.: US 6,428,757 B1
(45) Date of Patent: Aug. 6, 2002

(54) DEVICE FOR BRINGING SOLID BODIES IN THE FORM OF POURABLE PIECES INTO CONTACT WITH LIQUIDS AND POSSIBLY GASES

(75) Inventor: Gert Albert, Brunsbüttel (DE)

(73) Assignee: SASOL Germany GmbH (DE)

( * ) Notice: Subject to any disclaimer, the term of this patent is extended or adjusted under 35 U.S.C. 154(b) by 0 days.

(21) Appl. No.: 09/297,626

(22) PCT Filed: Oct. 29, 1997

(86) PCT No.: PCT/DE97/02564

§ 371 (c)(1),
(2), (4) Date: May 4, 1999

(87) PCT Pub. No.: WO98/19785

PCT Pub. Date: May 14, 1998

(30) Foreign Application Priority Data

Nov. 5, 1996 (DE) ......................................... 196 45 527

(51) Int. Cl.[7] .................................................. B01F 7/00
(52) U.S. Cl. ....................... 422/224; 422/225; 422/232; 422/238; 422/239; 422/270; 422/271
(58) Field of Search ................................. 422/238, 239, 422/224, 225, 194, 193, 215, 139, 232, 270, 271, 173, 174, 175, 209, 210, 217, 237, 266, 267, 268, 269, 222; 366/295, 293; 241/83, 84, 46.08, 46.13, 46.15; 165/8, 9

(56) References Cited

U.S. PATENT DOCUMENTS

| 3,888,973 A | * | 6/1975 | Colwell et al. | 423/493 |
| 4,590,289 A | | 5/1986 | Albert et al. | 556/188 |
| 5,479,851 A | * | 1/1996 | McClean et al. | 99/512 |
| 5,766,958 A | * | 6/1998 | Sullivan et al. | 436/174 |

FOREIGN PATENT DOCUMENTS

| AU | 688989 | 3/1998 |
| CH | 396902 | 1/1966 |
| JP | 61-293536 | 12/1986 |
| WO | WO 84/00953 | 3/1994 |

* cited by examiner

*Primary Examiner*—Jerry D. Johnson
*Assistant Examiner*—Frederick Varcoe
(74) *Attorney, Agent, or Firm*—Browning Bushman P.C.

(57) ABSTRACT

The instant invention relates to an apparatus for contacting solids in the form of flowable lumps with liquids and, optionally, gases, particularly for producing aluminum alcoholates by reacting aluminum with an excess of an aliphatic $C_3$ to $C_{10}$ alcohol, wherein solids charged to a reactor from the top are contacted in a spouted bed with liquid or a mixture of liquids and a rotary grate is provided for holding at least temporarily the aluminum lumps in the form of ingot off-cuts.

10 Claims, 1 Drawing Sheet

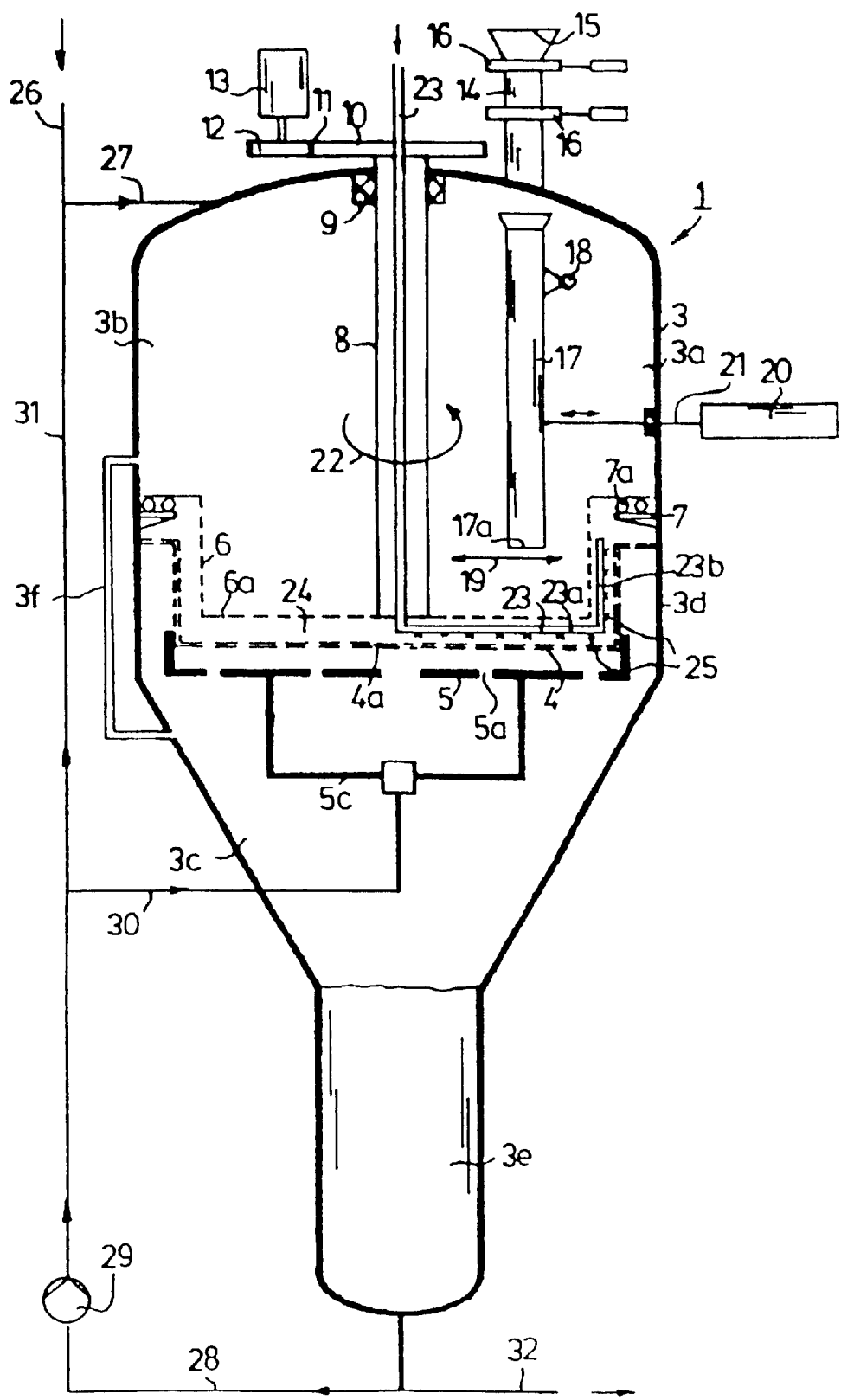

DEVICE FOR BRINGING SOLID BODIES IN THE FORM OF POURABLE PIECES INTO CONTACT WITH LIQUIDS AND POSSIBLY GASES

BACKGROUND OF THE INVENTION

1. Field of the Invention

The instant invention relates to an apparatus for contacting solids in the form of flowable lumps with liquids and, optionally, gases in order to dissolve said solids using a housing wherein a perforated vat holding the solids is disposed which, as the liquid flows around, forms a spouted bed.

2. Description of the Prior Art

DE 32 44 972 C1 (U.S. Pat. No. 4,590,289) discloses an apparatus comprising a reactor housing with a vat holding aluminium particles in the form of needles or chips arranged therein. An aluminium alcoholate/alcohol mixture is set bubbling such that the fine aluminium particles are whirled up in the screen basket whereby the aluminium dissolves in the aluminium alcoholate/alcohol mixture.

SUMMARY OF THE INVENTION

It is the object of the instant invention to increase the volume turnover of said reactor and to enable the use of lumpy solids, preferably ingot off-cuts.

According to the instant invention, the problem is solved by providing a rotary grate for holding the solids at least temporarily.

The volume turnover can be significantly increased by using said rotary grate. It is now possible to use large lumps, e.g. ingot off-cuts of more than 1 kg, which could not be used up to now.

According to another embodiment of this invention, there is provided a vertical pipe for placing the solids into the rotary grate, said pipe allowing to charge the solids from the top and to distribute them evenly in the screen reactor space. According to another embodiment of the instant invention, said vertical pipe is provided with a joint such that the lower pipe outlet can be shifted between edge and center of the rotary grate. Furthermore, the pipe is adjustable by means of a device which is steerable from outside.

According to another embodiment of the present invention, the basket-like rotary grate is disposed on a central, vertical shaft protruding from the top of the reactor. The protrusion point is sealed and the shaft can be rotated from outside the reactor using a motor.

According to another embodiment of this invention, the rotational speed of said rotary grate is adjustable such that the solids placed therein will be dissolved after a single turn of the grate.

According to another embodiment of the instant invention, the edge of said rotary grate is supported by a console mounted on the interior wall of the reactor. The rotary grate remains rotatable and, thus, is easy to manipulate.

According to another embodiment of the present invention, purifying jets are arranged around the rotary grate such that a cleaning fluid or fluid mixture can be sprayed onto the screen basket, thus preventing clogging of the meshes.

According to another embodiment of this invention, said purifying jets are arranged on a pipe which is led through the hollow shaft of the rotary grate into a space between screen basket and rotary grate and therefrom outside.

According to another embodiment of the instant invention, said pipe extends in the space from the outer end of a radial pipe section to an upward-bent pipe section.

BRIEF DESCRIPTION OF THE DRAWING

The instant invention is illustrated in greater detail by the attached drawing showing a reactor for producing an aluminium alcoholate/alcohol mixture, the reactor comprising a screen basket with a rotary grate disposed thereabove.

DESCRIPTION OF THE PREFERRED EMBODIMENT

The drawing shows a reactor 1 in a reactor housing 3. Inside the housing 3a, there is a screen basket 4 dividing the reactor into an upper section 3b and a lower section 3c. A connecting line 3f is provided for equalizing the pressure between lower section 3c and upper section 3b of the reactor. Said connecting line 3f is important for preventing disturbances in the screen basket 4 which may be caused by formation of reaction gas and vapor at the reactor bottom. The screen basket 4 has orifices 4a and is mounted (not depicted) on the wall 3d of the reactor housing 3. There is a vat 5 below the screen basket 4. Said vat, too, has orifices 5a. Several pipes 5c are led into the vat 5 for introducing an aluminium alcoholate/alcohol mixture which, as described hereinbelow, will bubble over the aluminium lumps placed in the vat, thus forming a spouted bed. There is a rotary grate 6 above the screen basket 4. Said rotary grate, too, is perforated 6a and supported by bearings 7a on a console 7.

The rotary grate 6 is connected to a hollow shaft 8 led via a bearing 9 with stuffing-box and slide-ring packing to the toothed wheel 10 of a gear 11. Said toothed wheel 10 of the gear 11 intermeshes with a toothed wheel 12 driven by a motor 13.

There is provided a feeding device 14 (not described in greater detail) through which, by means of a hopper 15, aluminium lumps, preferably ingot off-cuts (even those of more than 1 kilogram in weight), can be filled into the reactor. Said lumps fall through the feeder 14 into a vertical pipe 17, while passing several slides 16 which are opened and closed by turns. Said pipe 17 is disposed on a bearing 18 allowing to shift the lower outlet 17a of the pipe 17 from the center of the rotary grate 6 to its edges, as indicated by the bidirectional arrow 19. The vertical pipe 17 is shifted by means of an adjusting device 20 disposed outside the reactor and connected with the vertical pipe 17 by means of a rod 21.

A pipe 23 in the shaft 8 of the rotary grate 6 which is rotatable as indicated by the arrow 22 leads into a space 24 between rotary grate 6 and screen basket 4. The pipe 23 which is rotated with the shaft 8 is led to the edge of the interspace and upward. The pipe sections leading to the edge 23a of the interspace and then upward 23b are provided with purifying jets 25 directed at the screen basket 4.

Fresh hexanol can be charged to the reactor 1 via line 26. After charging the aluminium lumps through vertical pipe 17 onto rotary grate 6, the fresh hexanol flows through line 27 to the interior 3a of the reactor. The aluminium particles employed are very coarse, preferably ingot off-cuts. The space between rotary grate 6 and screen basket 4 is 5 to 10 cm. The speed of drive 11 and 13 is adjusted such that the solids charged through the vertical pipe 17 and evenly distributed on the rotary grate 6 will be dissolved after a single turn of the grate. It is important that the aluminium lumps charged through pipe 17 onto the rotary grate 6 form a layer which is for example 10 to 15 cm thick.

After start-up of the reactor, an aluminium alcoholate/alcohol mixture will collect in the lower part 3e of the reactor housing 3. Said mixture can be charged through lines 28 and 30, via pump 29, to the vat 5. The aluminium alcoholate/alcohol mixture is charged at high pressure such that the mixture is set bubbling, thus forming a spouted bed. The bubbling liquid flows through screen basket 4 and rotary grate 6 over the aluminium lumps in the reactor. Furthermore, the aluminum alcoholate/alcohol mixture flows through lines 31 and 27 to the upper part 3b of the reactor housing 3.

The mixture will immediately stop bubbling as the pump 29 is switched off. The liquid will drop to the lower part 3e of the reactor such that the aluminium lumps are no longer contacted by liquid. Thus, the reaction is suddenly interrupted.

Part of the aluminium alcoholate/alcohol mixture can be discharged via line 32.

The apparatus described hereinabove will allow an exceptionally high throughput. Existing reactors as the one disclosed in DE 32 44 972 C1 can readily be revamped as described herein in order to increase the conversion and allow the use of lumps.

What is claimed is:

1. An apparatus for contacting solids in the form of flowable lumps with liquids and, optionally, gases in order to dissolve said solids, comprising:
   a housing;
   a rotary grate disposed in said housing to hold the solids to be dissolved;
   a perforated vat disposed in the housing below the rotary grate to hold a spouted bed;
   pipes for supplying said liquids into the perforated vat in such a manner as to provide said spouted bed; and
   a screen basket disposed in the housing above said perforated vat and below said rotary grate.

2. The apparatus of claim 1 characterized in that there is a vertical pipe for placing the solids onto the rotary grate.

3. The apparatus of claim 2, characterized in that said vertical pipe is provided with a joint whereby the lower outlet of said vertical pipe can be shifted between the edge and the center of the rotary grate.

4. The apparatus of claim 3, characterized in that said vertical pipe is adjustable by means of a device that can be manipulated from outside said housing.

5. The apparatus of claim 1, characterized in that said rotary grate has the shape of a basket and is mounted on a central vertical shaft extending into said housing.

6. The apparatus of claim 5, characterized in that said shaft protrudes from the top of said housing through a seal, said shaft being rotatable by a motor mounted outside said housing.

7. The apparatus of claim 1, characterized in that the edge of the rotary grate is supported on a console mounted on the interior wall of the housing.

8. The apparatus of claim 1, characterized in that purifying jets are arranged around the rotary grate and are directed at the screen basket.

9. The apparatus of claim 1, characterized in that purifying jets are arranged around the rotary grate and are directed at the screen basket, said purifying jets being arranged on a rotating tube extending through said shaft and into a space between said screen basket and said rotary grate, said rotating tube having a generally vertical section extending exteriorally of said housing.

10. The apparatus of claim 9, characterized in that rotating tube further includes a lateral section extending from said vertical section to said space between said screen basket and said rotary grate and an upwardly extending section extending from said lateral section distal said vertical section.

* * * * *